US011041049B2

(12) United States Patent
Moser et al.

(10) Patent No.: US 11,041,049 B2
(45) Date of Patent: Jun. 22, 2021

(54) DUAL CURABLE THIOL-ENE COMPOSITION, COMPRISING A POLYTHIOL, AN UNSATURATED COMPOUND, A PHOTOINITIATOR AND AN ORGANIC HYDROPEROXIDE, AS WELL AS A CROSS-LINKED POLYMER SEALANT PREPARED THEREFROM FOR USE IN AEROSPACE

(71) Applicant: 3M INNOVATIVE PROPERTIES COMPANY, St. Paul, MN (US)

(72) Inventors: William H. Moser, Edina, MN (US); Erik M. Townsend, South St. Paul, MN (US); Brian S. Lam, Minneapolis, MN (US); Jonathan D. Zook, Stillwater, MN (US); Susan E. DeMoss, Stillwater, MN (US); Sheng Ye, Woodbury, MN (US); Andrew R. Davis, Catonsville, MD (US); Michael D. Swan, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/308,697

(22) PCT Filed: Jun. 27, 2017

(86) PCT No.: PCT/US2017/039383
§ 371 (c)(1),
(2) Date: Dec. 10, 2018

(87) PCT Pub. No.: WO2018/005416
PCT Pub. Date: Jan. 4, 2018

(65) Prior Publication Data
US 2019/0144610 A1 May 16, 2019

Related U.S. Application Data

(60) Provisional application No. 62/357,128, filed on Jun. 30, 2016.

(51) Int. Cl.
| | | |
|---|---|---|
| *C08G 75/04* | (2016.01) | |
| *C09J 181/02* | (2006.01) | |
| *C08G 75/045* | (2016.01) | |
| *C09K 3/10* | (2006.01) | |
| *C08G 75/12* | (2016.01) | |
| *C08L 81/02* | (2006.01) | |
| *C08G 75/32* | (2006.01) | |
| *C07D 277/82* | (2006.01) | |
| *B64C 3/34* | (2006.01) | |
| *B64C 1/12* | (2006.01) | |
| *B64C 1/14* | (2006.01) | |

(52) U.S. Cl.
CPC .......... *C08G 75/045* (2013.01); *C07D 277/82* (2013.01); *C08G 75/12* (2013.01); *C08G 75/32* (2013.01); *C08L 81/02* (2013.01); *C09J 181/02* (2013.01); *C09K 3/10* (2013.01); *C09K 3/1012* (2013.01); *B64C 1/12* (2013.01); *B64C 1/14* (2013.01); *B64C 3/34* (2013.01); *C08G 2190/00* (2013.01); *C09K 2003/1062* (2013.01)

(58) Field of Classification Search
CPC .......... B64C 1/14; B64C 3/34; C07D 277/82; C08G 75/045; C08G 75/12; C08G 75/32; C08G 2190/00; C08L 81/02; C09J 181/02; C08K 3/10; C08K 3/1012; C09K 2003/1062
See application file for complete search history.

(56) References Cited

U.S. PATENT DOCUMENTS

| | | | |
|---|---|---|---|
| 2,466,963 A | 4/1949 | Patrick et al. | |
| 2,789,958 A | 4/1957 | Fettes et al. | |
| 3,923,748 A | 12/1975 | Hutt et al. | |
| 4,165,425 A | 8/1979 | Bertozzi | |
| 4,366,307 A | 12/1982 | Singh et al. | |
| 4,609,762 A | 9/1986 | Morris et al. | |
| 4,808,638 A * | 2/1989 | Steinkraus | C08G 75/12 522/167 |
| 5,225,472 A | 7/1993 | Cameron et al. | |
| 5,610,243 A | 3/1997 | Vietti et al. | |
| 5,912,319 A | 6/1999 | Zook et al. | |
| 5,959,071 A | 9/1999 | DeMoss et al. | |
| 6,172,179 B1 | 1/2001 | Zook et al. | |
| 6,509,418 B1 | 1/2003 | Zook et al. | |

FOREIGN PATENT DOCUMENTS

| | | |
|---|---|---|
| JP | 2007002108 | 6/2005 |
| WO | WO 88/002879 | 4/1988 |
| WO | WO 2013/090988 | 6/2013 |
| WO | WO 2014/164244 | 10/2014 |
| WO | WO 2014/172305 | 10/2014 |
| WO | WO 2015/102967 | 7/2015 |
| WO | WO 2016/106352 | 6/2016 |

* cited by examiner

OTHER PUBLICATIONS

International Search report for PCT International Application No. PCT/US2017/039383 dated Sep. 12, 2017, pp. 6.

*Primary Examiner* — Sanza L. McClendon
(74) *Attorney, Agent, or Firm* — Philip P. Soo

(57) ABSTRACT

A dual curable thiol-ene composition comprising a polythiol, an unsaturated compound, a photoinitiator, an organic hydroperoxide (thermal initiator) and optionally a nitrogen-containing base, such as e.g. an N-heterocyclic compound (together with the organic hydroperoxide a redox initiator system). A cross-linked polymer prepared therefrom. A method of making such a polymer. A cured sealant comprising such a polymer. The sealant is preferably for use in aerospace.

17 Claims, 1 Drawing Sheet

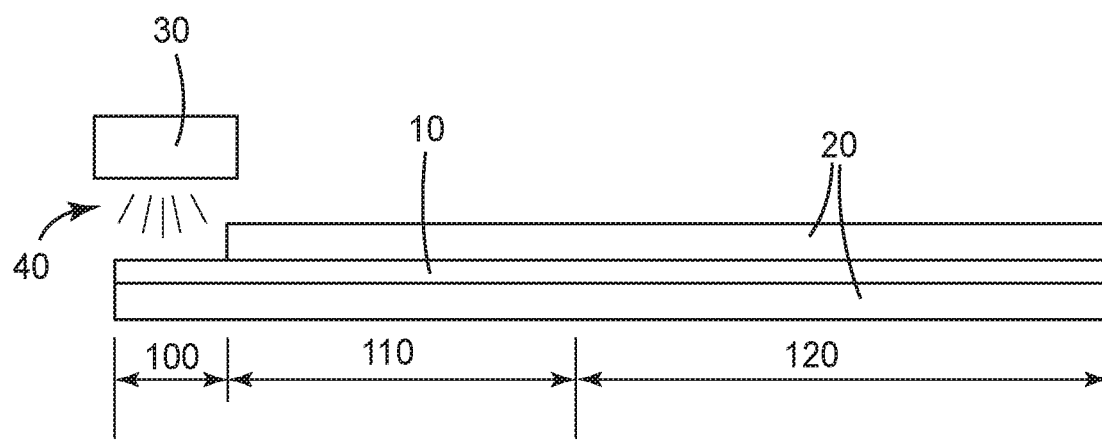

DUAL CURABLE THIOL-ENE COMPOSITION, COMPRISING A POLYTHIOL, AN UNSATURATED COMPOUND, A PHOTOINITIATOR AND AN ORGANIC HYDROPEROXIDE, AS WELL AS A CROSS-LINKED POLYMER SEALANT PREPARED THEREFROM FOR USE IN AEROSPACE

CROSS REFERENCE TO RELATED APPLICATIONS

This application is a national stage filing under 35 U.S.C. 371 of PCT/US2017/039383, filed Jun. 27, 2017, which claims the benefit of U.S. Provisional Application No. 62/357,128, filed Jun. 30, 2016, the disclosure of which are incorporated by reference in their entireties herein.

BACKGROUND

Sulfur-containing polymers are known to be well-suited for use in aerospace sealants due to their fuel resistant nature upon crosslinking. A desirable combination of properties for aerospace sealants, which is difficult to obtain, is the combination of long application time (i.e., the time during which the sealant remains usable) and short curing time (the time required to reach a predetermined strength).

Some sulfur-containing polymers useful as sealants are reported to be curable by exposure to light. See, for example, Int. Pat. Appl. Pub. Nos. WO 2014/164244 (Ye et al.), WO 2014/172305 (Zook et al.), and WO 2013/090988 (Bateman et al.).

U.S. Pat. No. 3,923,748 (Hutt) describes that alkaline initiators in the presence of tert-butyl perbenzoate can be useful for making mercaptan-terminated liquid polymers.

SUMMARY

Compositions and methods according to the present disclosure include a polythiol, at least one unsaturated compound having more than one carbon-carbon double bond, carbon-carbon triple bond, or a combination thereof; and two polymerization initiators. One initiator is a photoinitiator suitable for photochemically curing the composition by generating free radicals. The second initiator is a hydroperoxide suitable for curing the composition, for example, under ambient conditions. The photoinitiator provides a cure-on-demand feature to the composition according the present disclosure when the composition is exposed to a light trigger, for example, to provide at least a non-tacky surface or, in some cases, to fully cure the composition. The presence of the hydroperoxide in the composition provides several advantages. The hydroperoxide provides the composition with a backup curing mechanism and ensures curing in cases in which photochemical irradiation is not an option, does not reach the entire composition (e.g., in unexposed areas) or is inadvertently omitted. As shown in the Examples, below, the hydroperoxide does not interfere with the photochemical cure using the photoinitiator, and the presence of the photoinitiator does not interfere with the redox cure provided by the hydroperoxide. Thus, the composition can be useful, for example, as a one-part or two-part sealant composition with an optional cure-on-demand feature.

In one aspect, the present disclosure provides a composition including a polythiol, at least one unsaturated compound having more than one carbon-carbon double bond, carbon-carbon triple bond, or a combination thereof, a photoinitiator, and an organic hydroperoxide other than methyl ethyl ketone peroxide.

In another aspect, the present disclosure provides a composition including a polythiol, at least one unsaturated compound comprising more than one carbon-carbon double bond, carbon-carbon triple bond, or a combination thereof, a photoinitiator, an organic hydroperoxide, and a substituted or unsubstituted nitrogen-containing ring.

In another aspect, the present disclosure provides a cross-linked polymer preparable from the composition described above, wherein at least some of the thiol groups in the polythiol and carbon-carbon double bonds, carbon-carbon triple bonds, or a combination thereof have reacted to form thioether groups.

In another aspect, the present disclosure provides a method of making a polymer network. The method includes providing the composition described above and at least one of exposing the composition to light to at least partially cure the composition or allowing the composition to at least partially cure at ambient temperature.

In this application:

Terms such as "a", "an" and "the" are not intended to refer to only a singular entity, but include the general class of which a specific example may be used for illustration. The terms "a", "an", and "the" are used interchangeably with the term "at least one".

The phrase "comprises at least one of" followed by a list refers to comprising any one of the items in the list and any combination of two or more items in the list. The phrase "at least one of" followed by a list refers to any one of the items in the list or any combination of two or more items in the list.

The terms "cure" and "curable" refer to joining polymer chains together by covalent chemical bonds, usually via crosslinking molecules or groups, to form a network polymer. Therefore, in this disclosure the terms "cured" and "crosslinked" may be used interchangeably. A cured or crosslinked polymer is generally characterized by insolubility, but may be swellable in the presence of an appropriate solvent.

The term "polymer or polymeric" will be understood to include polymers, copolymers (e.g., polymers formed using two or more different monomers), oligomers or monomers that can form polymers, and combinations thereof, as well as polymers, oligomers, monomers, or copolymers that can be blended.

"Alkyl group" and the prefix "alk-" are inclusive of both straight chain and branched chain groups and of cyclic groups. In some embodiments, alkyl groups have up to 30 carbons (in some embodiments, up to 20, 15, 12, 10, 8, 7, 6, or 5 carbons) unless otherwise specified. Cyclic groups can be monocyclic or polycyclic and, in some embodiments, have from 3 to 10 ring carbon atoms. Terminal "alkenyl" groups have at least 3 carbon atoms.

"Alkylene" is the multivalent (e.g., divalent or trivalent) form of the "alkyl" groups defined above.

"Arylalkylene" refers to an "alkylene" moiety to which an aryl group is attached. "Alkylarylene" refers to an "arylene" moiety to which an alkyl group is attached.

The terms "aryl" and "arylene" as used herein include carbocyclic aromatic rings or ring systems, for example, having 1, 2, or 3 rings and optionally containing at least one heteroatom (e.g., O, S, or N) in the ring. Unless otherwise specified, aryl groups may have up to five substituents independently selected from the group consisting of alkyl groups having up to 4 carbon atoms (e.g., methyl or ethyl), alkoxy having up to 4 carbon atoms, halo (i.e., fluoro, chloro, bromo or iodo), hydroxy, or nitro groups. Examples of aryl groups include phenyl, naphthyl, biphenyl, fluorenyl as well as furyl, thienyl, pyridyl, quinolinyl, isoquinolinyl, indolyl, isoindolyl, triazolyl, pyrrolyl, tetrazolyl, imidazolyl, pyrazolyl, oxazolyl, and thiazolyl.

The term "heterocyclyl" includes non-aromatic rings or ring systems that contain at least one ring heteroatom (e.g., O, S, N). The heterocyclyl group may include 1, 2, or 3 rings and includes all of the fully saturated and partially unsaturated derivatives of the above mentioned aryl groups having at least one heteroatom.

For the purposes of this application, the term "open time" is used interchangeably with the term "application time" and is measured as described in the Examples.

All numerical ranges are inclusive of their endpoints and non-integral values between the endpoints unless otherwise stated (e.g., 1 to 5 includes 1, 1.5, 2, 2.75, 3, 3.80, 4, 5, etc.).

BRIEF DESCRIPTION OF THE DRAWING

FIG. 1 is a diagram representing the use of a composition according to the present disclosure as a sealant between two substrates.

DETAILED DESCRIPTION

With reference to FIG. 1, in some embodiments of a composition according to the present disclosure, the composition 10 is applied between opaque substrates 20. Light 40 from actinic light source 30 is used to initiate cure of at least a portion of composition 10 exposed to light 40 in exposed zone 100. However, composition 10 in dark zones 110 and 120 is not exposed to light 40. The hydroperoxide and in some embodiments the amine in the composition of the present disclosure allows the composition to cure in adjacent dark zones 110 and 120.

A variety of polythiols and unsaturated compounds comprising more than one carbon-carbon double bond, carbon-carbon triple bond, or a combination thereof may be useful in the compositions according to the present disclosure. In some embodiments, the polythiol is monomeric. In these embodiments, the polythiol may be an alkylene, arylene, alkylarylene, arylalkylene, or alkylenearylalkylene having more than one mercaptan group, wherein any of the alkylene, alkylarylene, arylalkylene, or alkylenearylalkylene are optionally interrupted by one or more ether (i.e., —O—), thioether (i.e., —S—), or amine (i.e., —NR$^1$—) groups and optionally substituted by alkoxy or hydroxyl. Useful monomeric polythiols may be dithiols or polythiols with more than 2 (in some embodiments, 3 or 4) mercaptan groups. In some embodiments, the polythiol is an alkylene dithiol in which the alkylene is optionally interrupted by one or more ether (i.e., —O—) or thioether (i.e., —S—) groups. Examples of useful dithiols include 1,2-ethanedithiol, 1,2-propanedithiol, 1,3-propanedithiol, 1,3-butanedithiol, 1,4-butanedithiol, 2,3-butanedithiol, 1,3-pentanedithiol, 1,5-pentanedithiol, 1,6-hexanedithiol, 1,3-dimercapto-3-methylbutane, dipentenedimercaptan, ethylcyclohexyldithiol (ECHDT), dimercaptodiethylsulfide, methyl-substituted dimercaptodiethylsulfide, dimethyl-substituted dimercaptodiethylsulfide, dimercaptodioxaoctane, 1,5-dimercapto-3-oxapentane and mixtures thereof. Polythiols having more than two mercaptan groups include propane-1,2,3-trithiol; 1,2-bis[(2-mercaptoethyl)thio]-3-mercaptopropane; tetrakis(7-mercapto-2,5-dithiaheptyl) methane; and trithiocyanuric acid. Combinations of any of these or with any of the dithiols mentioned above may be useful.

It should be understood that the unsaturated compound having carbon-carbon double bonds and/or carbon-carbon triple bonds are reactive and generally not part of an aromatic ring. In some of these embodiments, the carbon-carbon double and triple bonds are terminal groups in a linear aliphatic compound. However, styryl groups and allyl-substituted aromatic rings may be useful. The unsaturated compound may also include one or more ether (i.e., —O—), thioether (i.e., —S—), amine (i.e., —NR$^1$—), or ester (e.g., so that the compound is an acrylate or methacrylate) groups and one or more alkoxy or hydroxyl substituents. In some embodiments, the unsaturated compound does not include ester groups or carbonate groups. That is, the unsaturated compound is not an acrylate, methacrylate, vinyl ester, or vinyl carbonate. Unsaturated compounds without ester and carbonate groups may be more chemically stable than unsaturated compounds that contain these groups. Suitable unsaturated compounds include dienes, diynes, divinyl ethers, diallyl ethers, ene-ynes, and trifunctional versions of any of these. Combinations of any of these groups may also be useful.

Examples of suitable vinyl ethers having two or more vinyl ether groups include divinyl ether, ethylene glycol divinyl ether, butanediol divinyl ether, hexanediol divinyl ether, diethylene glycol divinyl ether, triethylene glycol divinyl ether, tetraethylene glycol divinyl ether, cyclohexanedimethanol divinyl ether, polytetrahydrofuryl divinyl ether, trimethylolpropane trivinyl ether, pentaerythritol tetravinyl ether, and combinations of any of these. Useful divinyl ethers of formula $CH_2=CH-O-(-R^2-O-)_m-CH=CH_2$, in which $R^2$ is $C_2$ to $C_6$ branched alkylene can be prepared by reacting a polyhydroxy compound with acetylene. Examples of compounds of this type include compounds in which $R^2$ is an alkyl-substituted methylene group such as —CH(CH$_3$)— (e.g., those obtained from BASF, Florham Park, N.J, under the trade designation "PLURIOL", for which $R^2$ is ethylene and m is 3.8) or an alkyl-substituted ethylene (e.g., —CH$_2$CH(CH$_3$)— such as those obtained from International Specialty Products of Wayne, N.J., under the trade designation "DPE" (e.g., "DPE-2" and "DPE-3").

Other suitable examples of unsaturated compounds having more than one carbon-carbon double bond or carbon-carbon triple bond include triallyl-1,3,5-triazine-2,4,6-trione, 2,4,6-triallyloxy-1,3,5-triazine, 4-vinyl-1-cyclohexene, 1,5-cyclooctadiene, 1,6-heptadiyne, 1,7-octadiyne, and diallyl phthalate. When using polythiols having two thiol groups, a mixture of unsaturated compounds may be useful in which at least one unsaturated compound has two carbon-carbon double or triple bonds, and at least one unsaturated compound has at least three carbon-carbon double or triple bonds. Mixtures of unsaturated compounds having at least 5 percent functional equivalents of carbon-carbon double or triple bonds contributed by polyenes having at least three carbon-carbon double or triple bonds may be useful.

Typically the amounts of the polythiol(s) and unsaturated compound(s) are selected for the curable composition so that there is a stoichiometric equivalence of mercaptan groups and carbon-carbon double and triple bonds.

In some embodiments, the polythiol in the curable composition according to the present disclosure is oligomeric or polymeric. Examples of useful oligomeric or polymeric polythiols include polythioethers and polysulfides. Polythioethers include thioether linkages (i.e., —S—) in their backbone structures. Polysulfides include disulfides linkages (i.e., —S—S—) in their backbone structures.

Polythioethers can be prepared, for example, by reacting dithiols with dienes, diynes, divinyl ethers, diallyl ethers, ene-ynes, or combinations of these under free-radical conditions. Useful reagents for making polythioethers include any of the dithiols, dienes, diynes, divinyl ethers, diallyl ethers, and ene-ynes listed above. Examples of useful polythioethers are described, for example, in U.S. Pat. No. 4,366,307 (Singh et al.), U.S. Pat. No. 4,609,762 (Morris et al.), U.S. Pat. No. 5,225,472 (Cameron et al.), U.S. Pat. No. 5,912,319 (Zook et al.), U.S. Pat. No. 5,959,071 (DeMoss et al.), U.S. Pat. No. 6,172,179 (Zook et al.), and U.S. Pat. No. 6,509,418 (Zook et al.). In some embodiments, the polythioether is represented by formula HS—$R^3$—[S—$(CH_2)_2$—O—[—$R^4$—O-]$_m$—$(CH_2)_2$—S—$R^3$-]$_n$—SH, wherein each $R^3$ and $R^4$ is independently a $C_{2-6}$ alkylene, which may be straight-chain or branched, $C_{6-8}$ cycloalkylene, $C_{6-10}$ alkylcycloalkylene, —[$(CH_2)_p$—X—]$_q$—(—$CH_2$—)$_r$, in which at least one —$CH_2$— is optionally substituted with a methyl group, X is one selected from the group consisting of O, S and —$NR^5$—, $R^5$ denotes hydrogen or methyl, m is a number from 0 to 10, n is a number from 1 to 60, p is a number from 2 to 6, q is a number from 1 to 5, and r is a number from 2 to 10. Polythioethers with more than two mercaptan groups may also be useful. Any of the free-radical initiators and methods described below in connection with at least partially curing the compositions disclosed herein may also be useful for preparing the polythioethers. In some embodiments, a thermal free-radical initiator described below is combined with the dithiols and dienes, diynes, divinyl ethers, diallyl ethers, ene-ynes, or combinations of these, and the resulting mixture is heated to provide the polythioethers.

Polythioethers can also be prepared, for example, by reacting dithiols with diepoxides, which may be carried out by stirring at room temperature, optionally in the presence of a tertiary amine catalyst (e.g., 1,4-diazabicyclo[2.2.2]octane (DABCO)). Useful dithiols include any of those described above. Useful epoxides can be any of those having two epoxide groups. In some embodiments, the diepoxide is a bisphenol diglycidyl ether, wherein the bisphenol (i.e., —O—$C_6H_5$—$CH_2$—$C_6H_5$—O—) may be unsubstituted (e.g., bisphenol F), or either of the phenyl rings or the methylene group may be substituted by halogen (e.g., fluoro, chloro, bromo, iodo), methyl, trifluoromethyl, or hydroxymethyl. Polythioethers prepared from dithiols and diepoxides have pendent hydroxyl groups and can have structural repeating units represented by formula —S—$R^3$—S—$CH_2$—CH(OH)—$CH_2$—O—$C_6H_5$—$CH_2$—$C_6H_5$—O—$CH_2$—CH(OH)—$CH_2$—S—$R^3$—S—, wherein $R^3$ is as defined above, and the bisphenol unit (i.e., —O—$C_6H_5$—$CH_2$—$C_6H_5$—O—) may be unsubstituted (e.g., bisphenol F), or either of the phenyl rings or the methylene group may be substituted by halogen (e.g., fluoro, chloro, bromo, iodo), methyl, trifluoromethyl, or hydroxymethyl. Mercaptan terminated polythioethers of this type can then optionally be reacted with any of the dienes, diynes, divinyl ethers, diallyl ethers, and ene-ynes listed above under free radical conditions. Any of the free-radical initiators and methods described below in connection with at least partially curing the composition disclosed herein may also be useful for preparing the polythioethers. In some embodiments, a thermal initiator described below is used, and the resulting mixture is heated to provide the polythioether.

The polythioethers may also be terminated with carbon-carbon double bonds, depending on the stoichiometry of the reaction. In these embodiments, the polythioethers can serve as the unsaturated compound having at least two carbon-carbon double bonds.

Polysulfides are typically prepared by the condensation of sodium polysulfide with bis-(2-chloroethyl) formal, which provides linear polysulfides having two terminal mercaptan groups. Branched polysulfides having three or more mercaptan groups can be prepared using trichloropropane in the reaction mixture. Examples of useful polysulfides are described, for example, in U.S. Pat. No. 2,466,963 (Patrick et al); U.S. Pat. No. 2,789,958 (Fettes et al); U.S. Pat. No. 4,165,425 (Bertozzi); and U.S. Pat. No. 5,610,243 (Vietti et al.). Polysulfides are commercially available under the trademarks "THIOKOL" and "LP" from Toray Fine Chemicals Co., Ltd., Urayasu, Japan and are exemplified by grades "LP-2", "LP-2C" (branched), "LP-3", "LP-33", and "LP-541".

Polythioethers and polysulfides can have a variety of useful molecular weights. In some embodiments, the polythioethers and polysulfides have number average molecular weights in a range from 500 grams per mole to 20,000 grams per mole, 1,000 grams per mole to 10,000 grams per mole, or 2,000 grams per mole to 5,000 grams per mole.

The polythioethers and polysulfides that are mercaptan-terminated may be combined with any of the unsaturated compounds including more than one carbon-carbon double or triple bonds described above using any of the free-radical initiators and methods described below to provide a cured composition according to the present disclosure.

The compositions according to the present disclosure can be at least partially cured using free-radical polymerization. Accordingly, compositions according to the present disclosure include a free-radical photoinitiator. In some embodiments, the free radical photoinitiator is a cleavage-type photoinitiator. Cleavage-type photoinitiators include acetophenones, alpha-aminoalkylphenones, benzoin ethers, benzoyl oximes, acylphosphine oxides and bisacylphosphine oxides and mixtures thereof. Examples of useful photoinitiators include benzoin ethers (e.g., benzoin methyl ether or benzoin butyl ether); substituted acetophenone (e.g., 2,2-dimethoxy-2-phenylacetophenone or 2,2-diethoxyacetophenone); 1-hydroxycyclohexyl phenyl ketone; and acylphosphonate derivatives (e.g., bis(2,4,6-trimethylbenzoyl) phenylphosphine oxide, diphenyl-2,4,6-trimethylbenzoylphosphine oxide, isopropoxyphenyl-2,4,6-trimethylbenzoylphosphine oxide, or dimethyl pivaloylphosphonate). Many photoinitiators are available, for example, from BASF under the trade designation "IRGACURE". The photoinitiator may be selected, for example, based on the desired wavelength for curing and compatibility with the curable composition. When using a photoinitiator, the composition is typically curable using an actinic light source. Two or more of any of these photoinitiators may also be used together in any combination.

Photoinitiators can be added in any amount suitable to initiate curing. In some embodiments, the photoinitiator is present in an amount in a range from 0.05 weight percent to about 5 weight percent (in some embodiments, 0.1 weight percent to 2.5 weight percent, or 0.1 weight percent to 2 weight percent).

Compositions according to the present disclosure also include an organic hydroperoxide. Organic hydroperoxides have the general structure R—OOH, wherein R is an alkyl group, aryl group, arylalkylene group, alkylarylene group, alkylarylenealkylene group, or a combination thereof. Examples of useful organic hydroperoxides include cumene hydroperoxide, tert-butyl hydroperoxide, tert-amyl hydroperoxide, 1,1,3,3-tetramethylbutyl hydroperoxide, isopropylcumyl hydroperoxide, p-menthane hydroperoxide (i.e., 1-methyl-1-(4-methylcyclohexyl)ethyl hydroperoxide), diisopropylbenzene hydroperoxide (e.g., 3,5-diisopropylhydroperoxide). In some embodiments, the organic hydroperoxide includes a ketone peroxide (e.g., methyl ethyl ketone peroxide, acetone peroxide, and cyclohexanone peroxide). In some embodiments, the organic hydroperoxide is other than methyl ethyl ketone peroxide. In some embodiments, the organic hydroperoxide is other than a ketone peroxide. Two or more of any of these organic hydroperoxides may also be used together in any combination. While organic hydroperoxides tend to be some of the more stable peroxides and require some of the highest temperatures for thermal initiation, in the presence of a polythiol and unsaturated compound in the composition of the present disclosure, the organic hydroperoxide can initiate curing at room temperature. This is shown in Examples 48 to 53 in the Examples, below. It is believed that polythiols can reduce organic hydroperoxides to generate radicals through a redox curing mechanism.

Organic hydroperoxides can be added in any amount suitable to initiate curing. In some embodiments, the organic hydroperoxide is present in an amount in a range from 0.05 weight percent to about 10 weight percent (in some embodiments, 0.1 weight percent to 5 weight percent, or 0.5 weight percent to 5 weight percent). In some embodiments, for example, when the amount of inorganic filler present in the composition is at least 25% or at least 30% by weight, the organic hydroperoxide can be present in an amount in a range from 1 weight percent to about 5 weight percent or about 2 weight percent to about 5 weight percent. The organic hydroperoxide and its amount may be selected to provide the composition with a desirable amount of open time (that is, the length of time it takes for the composition to become at least partially gelled) after it is mixed or thawed. In some embodiments, the composition has an open time of at least 10 minutes, at least 30 minutes, at least one hour, or at least two hours.

In some embodiments, compositions according to the present disclosure further comprise a nitrogen-containing base. In some embodiments, a combination of a nitrogen-containing base and an organic hydroperoxide can be considered a redox initiator. The nitrogen atom(s) in the nitrogen-containing base can be bonded to alkyl groups, aryl groups, arylalkylene groups, alkylarylene, alkylaryleneal-kylene groups, or a combination thereof. The nitrogen-containing base can also be a cyclic compound, which can include one or more rings and can be aromatic or non-aromatic (e.g., saturated or unsaturated). Cyclic nitrogen-containing bases can include a nitrogen as at least one of the atoms in a 5- or 6-membered ring. In some embodiments, the nitrogen-containing base includes only carbon-nitrogen, nitrogen-hydrogen, carbon-carbon, and carbon-hydrogen bonds. In some embodiments, the nitrogen-containing base can be substituted with at least one of alkoxy, aryl, arylalkylenyl, haloalkyl, haloalkoxy, halogen, nitro, hydroxy, hydroxyalkyl, mercapto, cyano, aryloxy, arylalkyleneoxy, heterocyclyl, or hydroxyalkyleneoxyalkylenyl.

In some embodiments, the nitrogen-containing base is a tertiary amine. Examples of useful tertiary amines include triethylamine, dimethylethanolamine, benzyldimethylamine, dimethylaniline, tribenzylamine, triphenylamine, N,N-dimethyl-para-toluidine, N,N-dimethyl-ortho-toluidine, tetramethylguanidine (TMG), 1,8-diazabicyclo[5.4.0]undec-7-ene (DBU), 1,5-diazabicyclo[4.3.0]non-5-ene (DBN), 1,4-diazabicyclo[2.2.2]octane (DABCO), quinuclidine, dimethylaminomethyl phenol, tris(dimethylaminomethyl) phenol, N,N-dihydroxyethyl-p-toluidine, N,N-diisopropylethylamine, and N,N,N',N'',N''-pentamethyl-diethylenetriamine. In some embodiments, the nitrogen-containing base is other than dihydroxyethyl-p-toluidine, N,N-diisopropyl-ethylamine, and N,N,N',N'',N''-pentamethyl-diethylenetriamine. Useful nitrogen-containing bases also include guanidines such as diphenylguanidine (DPG). In some embodiments, the nitrogen-containing base is a tertiary amines (including amidines) or guanidines.

In some embodiments, the nitrogen-containing base comprises a substituted or unsubstituted nitrogen-containing ring. In some embodiments, the substituted or unsubstituted nitrogen-containing ring has 5 or 6 atoms in the ring. The substituted or unsubstituted nitrogen-containing ring can be aromatic or nonaromatic and can have up to 4 nitrogen atoms in the ring. The ring can optionally include other heteroatoms (e.g., S and O). Substituted aromatic or non-aromatic rings can be substituted by one or more substituents independently selected from the group consisting of alkyl, aryl, arylalkylenyl, alkoxy, haloalkyl, haloalkoxy, halogen, nitro, hydroxy, hydroxyalkyl, mercapto, cyano, aryloxy, arylalkyleneoxy, heterocyclyl, hydroxyalkyleneoxyalkylenyl, amino, alkylamino, dialkylamino, (dialkylamino)alkyleneoxy, and oxo. The alkyl substituent can be unsubstituted or substituted by at least one of alkoxy having up to 4 carbon atoms, halo, hydroxy, or nitro. In some embodiments, the aryl or arylalkylenyl is unsubstituted or substituted by at least one of alkyl having up to 4 carbon atoms, alkoxy having up to 4 carbon atoms, halo, hydroxy, or nitro.

In some embodiments, the nitrogen-containing base is a substituted or unsubstituted pyridine, pyrazine, imidazole, pyrazole, tetrazole, triazole, oxazole, thiazole, pyrimidine, pyridazine, triazine, tetrazine, or pyrrole. Any of these may be substituted with halogen (e.g., iodo, bromo, chloro, fluoro), alkyl (e.g., having from 1 to 4, 1 to 3, or 1 to 2 carbon atoms), arylalkylenyl (e.g., benzyl), or aryl (phenyl). In some embodiments, the nitrogen-containing base, is a substituted or unsubstituted imidazole or pyrazole. The imidazole or pyrazole may be substituted with halogen (e.g., iodo, bromo, chloro, fluoro), alkyl (e.g., having from 1 to 4, 1 to 3, or 1 to 2 carbon atoms), arylalkylenyl (e.g., benzyl), or aryl (phenyl). Examples of useful nitrogen-containing rings include 1-benzylimidazole, 1,2-dimethylimidazole, 4-iodopyrazole, 1-methylbenzimidazole, 1-methylpyrazole, 3-methylpyrazole, 4-phenylimidazole, and pyrazole.

The nitrogen-containing base and its amount may be selected to provide the composition with a desirable amount of open time (that is, the length of time it takes for the composition to become at least partially gelled) after it is mixed or thawed. In some embodiments, the composition has an open time of at least 10 minutes, at least 30 minutes, at least one hour, or at least two hours. The amount of the nitrogen-containing base and its conjugate acid pKa can both affect the open time. A composition with a smaller amount of a nitrogen-containing base having a higher pKa may have the same open time as a composition having a larger amount of a nitrogen-containing base having a lower pKa. In some embodiments, the nitrogen-containing base is present in an amount in a range from 0.05 weight percent to about 10 weight percent (in some embodiments, 0.1 weight percent to 5 weight percent, or 0.5 weight percent to 5 weight percent). In some embodiments, for example, when the amount of inorganic filler present in the composition is at least 25% or at least 30% by weight, the nitrogen-containing base can be present in an amount in a range from 1 weight percent to about 5 weight percent or about 2 weight percent to about 5 weight percent.

As shown in the Examples below, the composition according to the present disclosure typically has an open time that can be useful for the production of very large structures, as is typical in the aircraft industry, and does not require heating above ambient conditions to cure. Thus, use of the composition as a sealant may avoid unpredictable performance that may be associated with overheating either the sealant material, the structure to be sealed, or both.

The compositions according to the present disclosure in any of their embodiments described above and below can be at least one of exposed to light for a sufficient time to at least partially cure the composition allowed to at least partially cure by the redox reaction of the organic hydroperoxide and the nitrogen-containing base. The method of making an at least partially crosslinked network according to the present disclosure includes providing a curable composition comprising a polythiol, at least one unsaturated compound comprising more than one carbon-carbon double bond, carbon-carbon triple bond, or a combination thereof, a photoinitiator, and an organic hydroperoxide. The method further includes subsequently at least one of exposing the composition to light or allowing the composition to at least partially cure without exposure to light under ambient conditions. In some embodiments, the method of making a polymer network includes exposing the composition disclosed herein in any of its embodiments to light. The light source and exposure time can be selected, for example, based on the nature and amount of the composition. Sources of ultraviolet and/or visible light can be useful (for example, wavelengths ranging from about 200 nm to about 650 nm, from about 315 nm to 550 nm, or from about 315 nm to 500 nm can be useful). Suitable light includes sunlight and light from artificial sources, including both point sources and flat radiators. In some embodiments, the composition is curable using a blue light source. In some embodiments, the composition is curable using a UV light source.

Examples of useful light sources include carbon arc lamps; xenon arc lamps; medium-pressure, high-pressure, and low-pressure mercury lamps, doped if desired with metal halides (metal halogen lamps); microwave-stimulated metal vapor lamps; excimer lamps; superactinic fluorescent tubes; fluorescent lamps; incandescent argon lamps; electronic flashlights; xenon flashlights; photographic flood lamps; light-emitting diodes; laser light sources (for example, excimer lasers); and combinations thereof. The distance between the light source and the curable composition can vary widely, depending upon the particular application and the type and/or power of the light source. For example, distances up to about 150 cm, distances from about 0.01 cm to 150 cm, or a distance as close as possible without touching the composition can be useful.

For any of the embodiments of the methods according to the present disclosure, exposing the composition to light at least partially cures the composition. The phrase "at least partially cured or crosslinked" includes the state where the molecular weight of the polymer network has increased via the formation of covalent bonds but before the overall system reaches the gelation point. Partially crosslinked polymers may have a measurable intrinsic viscosity in an appropriate solvent, as determined, for example, in accordance with ASTM Methods D1243, D1795, D2857, D4243 or D4603. Fully cured or crosslinked polymers will have an intrinsic viscosity too high to measure. The phrase "at least partially cured" encompasses partially crosslinked or cured polymer networks, polymer networks that have reached the gelation point, and fully cured compositions.

For any of the embodiments of the methods according to the present disclosure, exposing the composition to light at least partially cures the composition. In some of these embodiments, at least the surface of the composition is cured to an extent that the surface becomes non-tacky. A non-tacky surface may be one in which the surface no longer tightly adheres to L-LP-690 standard low density polyethylene film. Such a non-tacky surface may be achieved after exposure of the composition disclosed herein to a light source for up to 10 minutes, up to 5 minutes, up to 3 minutes, up to 2 minutes, or, in some cases, up to 1 minute, up to 30 seconds, up to 15 seconds, up to 5 seconds, or up to 1 second. Without exposure to light, in some embodiments, the composition according to the present disclosure exhibits at least one of a non-tacky surface or a 30 Shore "A" hardness in less than 24 hours, in some embodiments, less than 12 hours or 10 hours under ambient conditions. With or without exposure to light, in some embodiments, the compositions according to the present disclosure can achieve a 45 to 50 Shore "A" hardness in up to 2 weeks, up to 1 week, up to 5 days, up to 3 days, or up to 1 day.

In some embodiments, compositions according to the present disclosure may be useful in these applications, for example, because of their fuel resistance and low glass transition temperatures. In some embodiments, the polymer network according to the present disclosure has a low glass transition temperature, in some embodiments less than $-20°$ C., in some embodiments less than $-30°$ C., in some embodiments less than $-40°$ C., and in some embodiments less than $-50°$ C. In some embodiment, the polymer network according to the present disclosure has high jet fuel resistance, characterized by a volume swell of less than 30% and a weight gain of less than 20% when measured according to Society of Automotive Engineers (SAE) International Standard AS5127/1.

Crosslinked networks prepared with polythiols and compounds having two or more carbon-carbon double bonds, carbon-carbon triple bonds, or a combination thereof as described above in any of their embodiments are useful for a variety of applications. For example, such crosslinked networks can be useful as sealants, for example, aviation fuel resistant sealants. Aviation fuel resistant sealants are widely used by the aircraft industry for many purposes. Commercial and military aircraft are typically built by connecting a number of structural members, such as longitudinal stringers and circular frames. The aircraft skin, whether metal or composite, is attached to the outside of the stringers using a variety of fasteners and adhesives. These structures often include gaps along the seams, joints between the rigidly interconnected components, and overlapping portions of the exterior aircraft skin. The composition according to the present disclosure can be useful, for example, for sealing such seams, joints, and overlapping portions of the aircraft skin. The composition may be applied, for example, to aircraft fasteners, windows, access panels, and fuselage protrusions. As a sealant, the composition disclosed herein may prevent the ingress of weather and may provide a smooth transition between the outer surfaces to achieve desired aerodynamic properties. The composition according to the present disclosure may likewise be applied to interior assembles to prevent corrosion, to contain the various fluids and fuels necessary to the operation of an aircraft, and to allow the interior of the aircraft (e.g., the passenger cabin) to maintain pressurization at higher altitudes. Among these uses are the sealing of integral fuel tanks and cavities.

Aircraft exterior and interior surfaces, to which sealants may be applied, may include metals such as titanium, stainless steel, and aluminum, any of which may be anodized, primed, organic-coated or chromate-coated. For example, a dilute solution of one or more phenolic resins, organo-functional silanes, titanates or zirconantes, and a surfactant or wetting agent dissolved in organic solvent or water may be applied to an exterior or interior surface and dried.

Sealants may optionally be used in combination with a seal cap, for example, over rivets, bolts, or other types of fasteners. A seal cap may be made using a seal cap mold, filled with a curable sealant, and placed over a fastener. The curable sealant may then be cured. In some embodiments, the seal cap and the curable sealant may be made from the same material. In some embodiments, the seal cap may be made from a curable composition disclosed herein. For more details regarding seal caps, see, for example, Int. Pat. Appl. Pub. No. WO2014/172305 (Zook et al.).

When used in sealant applications, for example, compositions according to the present disclosure can also contain fillers, in some embodiments, inorganic fillers. However, unfilled compositions may also be useful in sealant applications. Conventional inorganic fillers such as silica (e.g., fumed silica), calcium carbonate, aluminum silicate, and carbon black may be useful as well as low density fillers. In some embodiments, the composition according to the present disclosure includes at least one of silica, hollow ceramic elements, hollow polymeric elements, calcium silicates, calcium carbonate, or carbon black. Calcium carbonate may be coated, for example, with a stearate coating. Silica, for example, can be of any desired size, including particles having an average size above 1 micrometer, between 100 nanometers and 1 micrometer, and below 100 nanometers. Silica can include nanosilica and amorphous fumed silica, for example. Suitable low density fillers may have a specific gravity ranging from about 1.0 to about 2.2 and are exemplified by calcium silicates, fumed silica, precipitated silica, and polyethylene. Examples include calcium silicate having a specific gravity of from 2.1 to 2.2 and a particle size of from 3 to 4 microns ("HUBERSORB HS-600", J. M. Huber Corp.) and fumed silica having a specific gravity of 1.7 to 1.8 with a particle size less than 1 ("CAB-O-SIL TS-720", Cabot Corp.). Other examples include precipitated silica having a specific gravity of from 2 to 2.1 ("HI-SIL TS-7000", PPG Industries), and polyethylene having a specific gravity of from 1 to 1.1 and a particle size of from 10 to 20 microns ("SHAMROCK S-395" Shamrock Technologies Inc.). The term "ceramic" refers to glasses, crystalline ceramics, glass-ceramics, and combinations thereof. Hollow ceramic elements can include hollow spheres and spheroids among other shapes. The hollow ceramic elements and hollow polymeric elements may have one of a variety of useful sizes but typically have a maximum dimension of less than 1 millimeter (mm). The specific gravities of the microspheres range from about 0.1 to 0.7 and are exemplified by polystyrene foam, microspheres of polyacrylates and polyolefins, and silica microspheres having particle sizes ranging from 5 to 100 microns and a specific gravity of 0.25 ("ECCOSPHERES", W. R. Grace & Co.). Other examples include elastomeric particles available, for example, from Akzo Nobel, Amsterdam, The Netherlands, under the trade designation "EXPANCEL". Yet other examples include alumina/silica microspheres having particle sizes in the range of 5 to 300 microns and a specific gravity of 0.7 ("FILLITE", Pluess-Stauffer International), aluminum silicate microspheres having a specific gravity of from about 0.45 to about 0.7 ("Z-LIGHT"), and calcium carbonate-coated polyvinylidene copolymer microspheres having a specific gravity of 0.13 ("DUALITE 6001AE", Pierce & Stevens Corp.). Further examples of commercially available materials suitable for use as hollow, ceramic elements include glass bubbles marketed by 3M Company, Saint Paul, Minn., as "3M GLASS BUBBLES" in grades K1, K15, K20, K25, K37, K46, S15, S22, S32, S35, S38, S38HS, S38XHS, S42HS, S42XHS, S60, S60HS, iM30K, iM16K, XLD3000, XLD6000, and G-65, and any of the HGS series of "3M GLASS BUBBLES"; glass bubbles marketed by Potters Industries, Carlstadt, N.J., under the trade designations "Q-CEL HOLLOW SPHERES" (e.g., grades 30, 6014, 6019, 6028, 6036, 6042, 6048, 5019, 5023, and 5028); and hollow glass particles marketed by Silbrico Corp., Hodgkins, Ill. under the trade designation "SIL-CELL" (e.g., grades SIL 35/34, SIL-32, SIL-42, and SIL-43). Such fillers, alone or in combination, can be present in a sealant in a range from 10 percent by weight to 55 percent by weight, in some embodiments, 20 percent by weight to 50 percent by weight, based on the total weight of the sealant composition.

When used in sealant applications, for example, compositions according to the present disclosure can also contain at least one of cure accelerators, surfactants, adhesion promoters, thixotropic agents, pigments, dyes, and solvents.

In these embodiments, the composition according to the present disclosure can include any suitable solvent or solvents capable of dissolving the components. The components may be present in the solvent at any suitable concentration, (e.g., from about 5 percent to about 90 percent by weight based on the total weight of the solution). Illustrative examples of suitable solvents include aliphatic and alicyclic hydrocarbons (e.g., hexane, heptane, and cyclohexane), aromatic solvents (e.g., benzene, toluene, and xylene), ethers (e.g., diethyl ether, glyme, diglyme, and diisopropyl ether), esters (e.g., ethyl acetate and butyl acetate), alcohols (e.g., ethanol and isopropyl alcohol), ketones (e.g., acetone, methyl ethyl ketone, and methyl isobutyl ketone), sulfoxides (e.g., dimethyl sulfoxide), amides (e.g., N,N-dimethylformamide and N,N-dimethylacetamide), halogenated solvents (e.g., methylchloroform, 1,1,2-trichloro-1,2,2-trifluoroethane, trichloroethylene, and trifluorotoluene), and mixtures thereof.

Pigments and dyes can be added to the composition in any suitable form, such as discrete particles, dispersions, solutions, flakes, and combinations thereof. A single colorant (including pigments and dyes) or a mixture of two or more colorants can be used in the coatings of the present invention. Example pigments include carbazole dioxazine crude pigment, azo, monoazo, diazo, naphthol AS, salt type (flakes), benzimidazolone, isoindolinone, isoindoline and polycyclic phthalocyanine, quinacridone, perylene, perinone, diketopyrrolo pyrrole, thioindigo, anthraquinone, indanthrone, anthrapyrimidine, flavanthrone, pyranthrone, anthanthrone, dioxazine, triarylcarbonium, quinophthalone pigments, diketo pyrrolo pyrrole red ("DPPBO red"), iron (III) hexacyanoferrate(II) (Prussian Blue), titanium dioxide, carbon black and mixtures thereof. Example dyes include those that are solvent and/or aqueous based such as phthalo green or blue, iron oxide, bismuth vanadate, anthraquinone, perylene, and quinacridone.

In some embodiments, the composition according to the present disclosure does not include a dye represented by formula

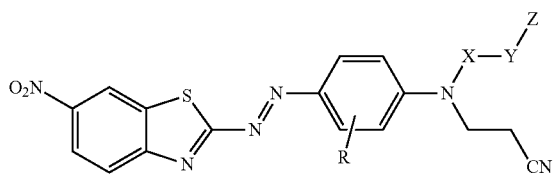

wherein
R is hydrogen or alkyl;
X is alkylene;
Y is a bond, ether, thioether, amine, amide, ester, thioester, carbonate, thiocarbonate, carbamate, thiocarbamate, urea, thiourea, alkylene, arylalkylene, alkylarylene, or arylene, wherein alkylene, arylalkylene, alkylarylene, and arylene are optionally at least one of interrupted or terminated by at least one of an ether, thioether, amine, amide, ester, thioester, carbonate, thiocarbonate, carbamate, thiocarbamate, urea, or thiourea; and
Z is an acrylate, a methacrylate, an acrylamide, a methacrylamide, a styrenyl, or a terminal alkenyl having at least three carbon atoms.

In some embodiments, the composition according to the present disclosure does not include a dye compound represented by formula:

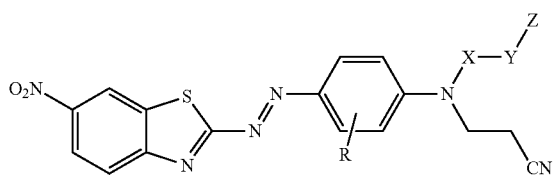

wherein
R is hydrogen or alkyl;
X is alkylene optionally interrupted by —O—;
Y is a bond, —O—, —S—, —NR$^1$—, —N(R$^1$)—C(O)—, —C(O)—N(R$^1$)—, —O—C(O)—, —C(O)—O—, —S—C(O)—, —C(O)—S—, —O—C(S)—, —C(S)—O—, —O—C(O)—O—, —S—C(O)—O—, —O—C(O)—S—, —(R$^1$)N—C(O)—O—, —O—C(O)—N(R$^1$)—, —(R$^1$)N—C(S)—O—, —O—C(S)—N(R$^1$)—, —N(R$^1$)—C(O)—S—, —S—C(O)—N(R$^1$)—, —(R$^1$)N—C(O)—N(R$^1$)—, or —(R$^1$)N—C(S)—N(R$^1$)—;
R$^1$ is hydrogen, alkyl, aryl, arylalkylenyl, or alkylarylenyl; and
Z is hydrogen, alkyl, aryl, arylalkylenyl, alkylarylenyl, heterocyclyl, or heterocyclylalkylenyl, wherein alkyl, aryl, arylalkylenyl, alkylarylenyl, heterocyclyl, or heterocyclylalkylenyl are unsubstituted or substituted by at least one substituent selected from the group consisting of alkyl, alkoxy, hydroxyalkyl, haloalkyl, haloalkoxy, halogen, nitro, hydroxyl, cyano, amino, alkylamino, dialkylamino, and in the case of alkyl, heterocyclyl, and heterocyclylalkylenyl, oxo.

Existing sealant products now in use in the aircraft industry are typically either two-part products or one-part products. For the two-part products, once the user mixes the two parts, the reaction begins and the sealant starts to form into an elastomeric solid. After mixing, the time that the sealant remains usable is called the application time. Throughout the application time, viscosity of the sealant gradually increases until the sealant is too viscous to be applied. Application time and cure time are typically related in that short application time products cure quickly. Conversely, long application time products cure slowly. In practice, customers choose products with differing application times and cure times depending on the specific application. This requires the customer to maintain inventories of multiple products to address the production flow requirements of building and repairing aircraft. For one-part products, users can avoid a complicated mixing step, but the product has to be shipped and stored in a freezer before application. Advantageously, in many embodiments, compositions according to the present disclosure can be useful as one-part or two-part sealants that can simultaneously have a long application time but can be cured on demand.

In some embodiments, the combination of an organic hydroperoxide and a nitrogen-containing base allows for a more desirable cure speed and more desirable final properties in the polymer network than when an organic peroxide is used. For example, Comparative Example B, which uses benzoyl peroxide, only has 30 minutes of open time while Examples 3 and 6, which use hydroperoxides and a 1-benzylimidazole, have an open time of 120 minutes.

Some Embodiments of the Disclosure

In a first embodiment, the present disclosure provides a composition comprising:
a polythiol;
at least one unsaturated compound comprising more than one carbon-carbon double bond, carbon-carbon triple bond, or a combination thereof;
a free-radical generating photoinitiator; and an organic hydroperoxide other than methyl ethyl ketone peroxide.

In a second embodiment, the present disclosure provides the composition of the first embodiment, further comprising a nitrogen-containing base.

In a third embodiment, the present disclosure provides the composition of the second embodiments, wherein the nitrogen-containing base is a tertiary amine.

In a fourth embodiment, the present disclosure provides the composition of the second or third embodiment, wherein the nitrogen-containing base comprises a substituted or unsubstituted nitrogen-containing ring.

In a fifth embodiment, the present disclosure provides a composition comprising:
a polythiol;
at least one unsaturated compound comprising more than one carbon-carbon double bond, carbon-carbon triple bond, or a combination thereof;
a free-radical generating photoinitiator;
an organic hydroperoxide; and
a substituted or unsubstituted nitrogen-containing ring.

In a sixth embodiment, the present disclosure provides the composition of the fourth or fifth embodiments, wherein the nitrogen-containing ring is a pyridine, pyrazine, imidazole, pyrazole, tetrazole, triazole, oxazole, thiazole, pyrimidine, pyridazine, triazine, tetrazine, or pyrrole.

In a seventh embodiment, the present disclosure provides the composition of the sixth embodiment, wherein the nitrogen-containing ring is an imidazole or pyrazole.

In an eighth embodiment, the present disclosure provides the composition of any one of the fourth to seventh embodiments, wherein the nitrogen-containing ring is unsubstituted or substituted with at least one halogen, alkyl, arylalkylenyl, or aryl.

In a ninth embodiment, the present disclosure provides the composition of any one of the first to eighth embodiments, wherein the organic hydroperoxide comprises at least one of cumene hydroperoxide, tert-butyl hydroperoxide, or tert-amyl hydroperoxide.

In a tenth embodiment, the present disclosure provides the composition of any one of the first to ninth embodiments, wherein the organic hydroperoxide is reduced to generate free-radicals.

In an eleventh embodiment, the present disclosure provides the composition of any one of the first to tenth embodiments, wherein the photoinitiator is a cleavage-type photoinitiator.

In a twelfth embodiment, the present disclosure provides the composition of the eleventh embodiment, wherein the photoinitiator comprises at least one of a benzoin ether, a substituted acetophenone, 1-hydroxycyclohexyl phenyl ketone, a substituted acylphosphine oxide, or a substituted acylphosphonate.

In a thirteenth embodiment, the present disclosure provides the composition of any one of the first to twelfth embodiments, wherein the polythiol is monomeric.

In a fourteenth embodiment, the present disclosure provides the composition of any one of the first to twelfth embodiments, wherein the polythiol is oligomeric or polymeric.

In a fifteenth embodiment, the present disclosure provides the composition of the fourteenth embodiment, wherein the polythiol is a polythioether oligomer or polymer or a polysulfide oligomer or polymer.

In a sixteenth embodiment, the present disclosure provides the composition of the fourteenth embodiment, wherein the polythiol is a polythioether oligomer or polymer prepared from components comprising a dithiol and a diene or divinyl ether and optionally a trithiol, triene, or trivinyl ether.

In a seventeenth embodiment, the present disclosure provides the composition of any one of the first to sixteenth embodiments, wherein the at least one unsaturated compound comprises two carbon-carbon double bonds, and wherein the curable composition further comprises a second unsaturated compound comprising three carbon-carbon double bonds.

In an eighteenth embodiment, the present disclosure provides the composition of any one of the first to the seventeenth embodiments, wherein the at least one unsaturated compound comprising more than one carbon-carbon double bond, carbon-carbon triple bond, or a combination thereof comprises at least one of a diene, a diyne, a divinyl ether, a diallyl ether, or an ene-yne.

In a nineteenth embodiment, the present disclosure provides the composition of any one of the first to sixteenth embodiments, wherein the unsaturated compound comprises three carbon-carbon double bonds.

In a twentieth embodiment, the present disclosure provides the composition of any one of the first to nineteenth embodiments, further comprising inorganic filler.

In a twenty-first embodiment, the present disclosure provides the composition of the twentieth embodiment, wherein the inorganic filler comprises at least one of silica, carbon black, calcium carbonate, aluminum silicate, or lightweight particles having a density of up to 0.7 grams per cubic centimeter.

In a twenty-second embodiment, the present disclosure provides the composition of any one of the first to nineteenth embodiments, further comprising at least one of a surfactant, adhesion promoter, thixotropic agent, pigment, dye, or solvent.

In a twenty-third embodiment, the present disclosure provides a method of making a polymer network, the method comprising:
providing the composition of any one of the first to twenty-second embodiments;
and at least one of:
exposing the composition to light to at least partially cure the composition; or
allowing the composition to at least partially cure at ambient temperature.

In a twenty-fourth embodiment, the present disclosure provides the method of the twenty-third embodiment, wherein the light comprises at least one of ultraviolet light or blue light.

In a twenty-fifth embodiment, the present disclosure provides the method of the twenty-fourth embodiment, wherein the light comprises blue light.

In a twenty-sixth embodiment, the present disclosure provides the method of any one of the twenty-third to twenty-fifth embodiments, wherein exposing the composition to light to at least partially cure the composition comprises at least partially gelling the composition.

In a twenty-seventh embodiment, the present disclosure provides the method of any one of the twenty-third to twenty-fifth embodiments, wherein exposing the composition to light to at least partially cure the composition comprises fully curing the composition.

In a twenty-eighth embodiment, the present disclosure provides a polymer network preparable from the composition of any one of the first to twenty-second embodiments, wherein at least some of the thiol groups in the polythiol and carbon-carbon double bonds, carbon-carbon triple bonds, or a combination thereof have reacted to form thioether groups.

In a twenty-ninth embodiment, the present disclosure provides a sealant comprising the polymer network of the twenty-eighth embodiment.

In a thirtieth embodiment, the present disclosure provides the sealant of the twenty-ninth embodiment, wherein the sealant is cured.

In order that this disclosure can be more fully understood, the following examples are set forth. It should be understood that these examples are for illustrative purposes only, and are not to be construed as limiting this disclosure in any manner.

EXAMPLES

Unless otherwise noted, all reagents were obtained or are available from Sigma-Aldrich Company, St. Louis, Mo., or may be synthesized by known methods. Unless otherwise reported, all ratios are by weight percent.

The following abbreviations are used to describe the examples:
° C.: degrees Centigrade
cm: centimeter
hrs: hours
kPa: kiloPascal
LED: light-emitting diode
mL: milliliter
Mn: molecular weight
N: Newton
nm: nanometer
psi: pounds per square inch sec: second The reference to (hydro)peroxide in the Tables refers to hydroperoxide or peroxide.

Materials.

Abbreviations for the materials used in the examples are as follows:

A-R202: A hydrophilic fumed silica, obtained under the trade designation "AEROSIL R202" from Evonik Industries AG, Essen, Germany.

1-BI: 1-Benzylimidazole, obtained from Alfa Aesar, Ward Hill, Mass.

1-BMI: 1-Benzyl-2-methylimidazole, obtained from TCI Co., Tokyo, Japan.

BPO: Benzoyl peroxide, obtained from Sigma-Aldrich Company.

CHP: Cumene hydroperoxide, technical grade, obtained from Alfa Aesar.

CMP: 3-Chloro-2-methyl-1-propene, obtained from Sigma-Aldrich Company.

DABCO: 1,4-Diazabicyclo[2.2.2]octane, obtained under the trade designation "DABCO" from Air Products & Chemicals, Inc., Allentown, Pa.

DMA: N,N-dimethylaniline, obtained from Sigma-Aldrich Company.

DMDO: 1,8-Dimercapto-3,6-dioxaoctane, obtained from Arkema, Inc., King of Prussia, Pa.

DMI: 1,2-Dimethylimidazole, obtained from TCI America, Portland, Oreg.

DMPT: N,N-Dimethyl-para-toluidine, obtained from Sigma-Aldrich Company.

DVE-3: Triethyleneglycol divinylether, obtained under the trade designation "RAPI-CURE DVE-3" from Ashland Specialty Ingredients, Wilmington, Del.

E-8220: A diglycidylether of bisphenol F, obtained under the trade designation "EPALLOY 8220" from Emerald Performance Materials, LLC, Cuyahoga Falls, Ohio.

FEB: Iron(III) hexacyanoferrate(II), obtained from Sigma-Aldrich Company.

I-819: Phenylbis(2,4,6-trimethylbenzoyl)phosphine oxide, obtained under the trade designation "IRGACURE 819" from BASF Corp., Florham Park, N.J.

4-IP: 4-Iodopyrazole, obtained from Sigma-Aldrich Company

MEKP: Methyl ethyl ketone peroxide, obtained from Sigma-Aldrich Company.

1-MB: 1-Methylbenzimidazole, obtained from Sigma-Aldrich Company

1-MP: 1-Methylpyrazole, obtained from Alfa Aesar.

3-MP: 3-Methylpyrazole, obtained from Aldrich Chemicals.

4-PI: 4-Phenylimidazole, obtained from Aldrich Chemicals.

Pyrazole: Obtained from Eastman Organic Chemicals, Rochester, N.Y.

SOCAL: Nanoparticle (70-100 nm) calcium carbonate, obtained under the trade designation "SOCAL 322" from Solvay Chemicals, Inc., Houston, Tex.

TAC: Triallylcyanurate, obtained from Sartomer, Inc., Exton, Pa.

TBHP: Tert-Butyl hydrogen peroxide, 70% aqueous solution, obtained from Alfa Aesar.

TBPO: Tert-Butyl peroxide, obtained from Sigma-Aldrich Company.

TVCH: 1,2,4-Trivinylcyclohexane, obtained from BASF Corp., Florham Park, N.J.

VAZO 52: 2,2'-Azobis(2,4-dimethyl-pentanenitrile), obtained under the trade designation "VAZO 52" from E.I. du Pont de Nemours and Company, Wilmington, Del.

Intermediates CMP Diene and polythioethers, PTE-1 and PTE-2, were synthesized as follows: CMP Diene (4,13-dithia-7,10-dioxa-2,15-dimethylhexadecyl-1,15-diene)

Into a 500 mL four-neck, round bottom flask fitted with a stirrer, thermometer, chilled water condenser and a pressure equalizing addition funnel was added 206.54 grams of a 20% aqueous solution of sodium hydroxide (1.033 moles). To this was added, dropwise with stirring, 94.08 grams (0.51 moles) DMDO, and the mixture then allowed to cool to approximately 21° C. 96.4 grams (1.065 moles) CMP was added dropwise with vigorous stirring, and stirring continued for another 2 hours. The mixture was then held at 21° C. for approximately 16 hours, after which 150 grams of a clear layer was decanted. NMR analysis confirmed the decanted layer to be CMP diene.

PTE-1

Into a 100-mL round bottom flask equipped with an air-driven stirrer, thermometer, and a dropping funnel, was added 37.33 grams (0.207 mole) DMDO and 3.99 grams (0.0122 mole) E-8220; To this mixture was added 0.02 grams DABCO. The system was flushed with nitrogen, then mixed and heated for 1.5 hours at 60-70° C. 12.81 grams (0.0438 mole) CMP diene was added along with approximately 0.01 grams VAZO 52. The material was mixed and heated to 60° C. and held at this temperature for 1.5 hrs. 0.64 grams (0.0039 mole) of TVCH was added and heating continued for another 1.5 hrs. 25.23 grams (0.125 mole) DVE-3 was then added drop-wise to the flask over a period of 45-60 minutes whilst maintaining the temperature at approximately 70° C. VAZO 52 was added in approximately 0.01 gram units over approximately 16 hrs, for a total of about 0.4 grams. The temperature was raised to 100° C. and the material degassed for approximately 10 minutes. The resultant polythioether was approximately 5062 Mn with 2.25 functionality.

PTE-2:

Into a 100-ml round bottom flask equipped with an air-driven stirrer, thermometer, and a dropping funnel, was added 39.64 grams (0.22 mole) DMDO and 4.10 grams (0.0125 mole) E-8220; To this mixture was added 0.02 grams DABCO. The system was flushed with nitrogen, then mixed and heated for 1.5 hours at 60-70° C. 3.66 grams (0.0125 mole) CMP diene was added along with approximately 0.01 grams VAZO 52. The material was mixed and heated to 60° C. and held at this temperature for 1.5 hrs. 0.83 g (0.005 mole) of TVCH was added and heating continued for another 1.5 hrs. 31.80 grams (0.157 moles) DVE-3 was then added drop-wise to the flask over a period of 45-60 minutes, whilst maintaining the temperature at approximately 70° C. VAZO 52 was added in approximately 0.01 gram units over approximately 16 hours, for a total of about 0.4 grams. The temperature was raised to 100° C. and the material degassed for approximately 10 minutes. The resultant polythioether was approximately 3200 Mn with 2.2 functionality.

Curing Lamps

CT2000: A 455 nm LED light, model "CT2000 LED", obtained from Clearstone Technologies, Inc., Hopkins, Minn.

S-10: A 450 nm dental curing lamp, obtained under the trade designation "ELIPAR S-10" from 3M Company, St. Paul, Minn.

Test Methods

Hardness

Hardness was measured using a model "DD-A" durometer, obtained from PCE America, Inc., Jupiter, Fla. Minimum sample thickness was 0.6 cm.

Open Time

Open time refers to the approximate amount of time the sealant composition exhibits sufficient flow in order to completely wet out a surface when manually spread with a spatula at 21° C.

Redox Cure

The sealant composition was held in the sample cup for 48 hours at 21° C., after which the hardness was measured. Preferably, the sample should have a Shore A value of greater than 30.

Photo Cure

Approximately 0.2 grams of the sealant composition was spread onto a mixing pad, irradiated using the Elipar S-10 lamp at a distance of approximately 1 cm for the specified amount of time, after which the hardness was measured. Preferably, the sample should have a Shore A value of greater than 30.

Tensile Strength and Elongation

The sealant composition was spread into two 8.8 by 3.1 by 0.25 cm Teflon™ molds at 21° C. The first sample was allowed to cure in the dark for one week. The second sample was exposed to the 455 nm, CT-2000 lamp, at 50% power at a distance of approximately 1.5 cm for 1 minute, after which it was also allowed to cure in the dark for one week. The cured samples were then removed from the molds and 6.2 by 1.0 cm by 0.3 cm neck, dog-bone shaped specimens were die-cut from the cured sample. Peak tensile strength and elongation were measured at a pull rate of 1-inch (2.54 cm)/min and a 400N load cell, using a model "INSTRON 5544" Tensile Strength Tester obtained from Instron Instruments, Norwood, Mass. Results reported herein represent an average of 3 cured samples per test.

Example 1

3.353 grams of TAC were added to 4.080 grams DVE-3 in a 50 mL round-bottomed flask and mixed by means of a magnetic stir bar at 21° C. until homogeneous. 0.12 grams of this mixture was then transferred to a 10 gram mixing cup, to which 2.83 grams PTE-1 and 0.05 grams CHP were added, and homogeneously dispersed for 30 seconds at 1,600 rpm using a model DAC 600 SpeedMixer, from FlackTek, Inc., Landrum, S.C. 0.029 grams base compound were added to the cup and manually stirred for approximately 1 minute.

Examples 2-12 and Comparatives A-C

The procedure generally described for preparing Example 1 was repeated, according to the compositions listed in Table 1. Open Times and Redox Cure results are listed in Table 2.

A photoinitiator can be added to the compositions to make Examples 1 to 12.

TABLE 1

| Composition | Composition | | Quantities (grams) | | | |
|---|---|---|---|---|---|---|
| | (Hydro)peroxide | Base | PTE-1 | (Hydro)Peroxide | DVE-3/TAC | Base |
| Example 1 | CHP | DMI | 2.83 | 0.05 | 0.12 | 0.029 |
| Example 2 | CHP | Pyrazole | 2.83 | 0.05 | 0.12 | 0.020 |
| Example 3 | CHP | 1-BI | 2.83 | 0.05 | 0.12 | 0.047 |
| Example 4 | TBHP | DMI | 2.85 | 0.03 | 0.12 | 0.029 |
| Example 5 | TBHP | Pyrazole | 2.85 | 0.03 | 0.12 | 0.020 |
| Example 6 | TBHP | 1-BI | 2.85 | 0.03 | 0.12 | 0.047 |
| Example 7 | MEKP | DMI | 2.82 | 0.06 | 0.12 | 0.029 |
| Example 8 | MEKP | Pyrazole | 2.82 | 0.06 | 0.12 | 0.020 |
| Example 9 | MEKP | 1-BI | 2.82 | 0.06 | 0.12 | 0.047 |
| Example 10 | CHP | DMA | 2.83 | 0.06 | 0.12 | 0.056 |
| Example 11 | CHP | DMA | 2.83 | 0.11 | 0.12 | 0.112 |
| Example 12 | CHP | DMA | 2.83 | 0.17 | 0.12 | 0.168 |
| Comparative A | BPO | DMPT | 2.83 | 0.02 | 0.17 | 0.190 |
| Comparative B | BPO | DMPT | 2.83 | 0.02 | 0.17 | 0.093 |
| Comparative C | BPO | DMPT | 2.83 | 0.01 | 0.17 | 0.190 |

TABLE 2

| Composition | Open time (min) | Redox Cure Shore A > 30 @ 48 hrs. |
|---|---|---|
| Example 1 | 60 | Yes |
| Example 2 | 120 | Yes |
| Example 3 | 120 | Yes |
| Example 4 | 60 | Yes |
| Example 5 | 120 | Yes |
| Example 6 | 140 | Yes |
| Example 7 | 120 | No |
| Example 8 | 60 | No |
| Example 9 | 90 | No |
| Example 10 | 100 | No |
| Example 11 | 80 | No |
| Example 12 | 60 | No |
| Comparative A | 15 | Yes |
| Comparative B | 30 | Yes |
| Comparative C | 180 | No |

Examples 13-18

The procedure generally described for preparing Example 1 was repeated, according to the compositions listed in Table 3. Open Times and Redox Cure results are listed in Table 4.

A photoinitiator can be added to the compositions to make Examples 13 to 18.

TABLE 3

| | Composition | | | | | |
|---|---|---|---|---|---|---|
| | | | Quantities (grams) | | | |
| Composition | Hydro-peroxide | Base | PTE-1 | Hydro-peroxide | DVE-3/TAC | Base |
| Example 13 | CHP | 1-BI | 2.84 | 0.04 | 0.12 | 0.047 |
| Example 14 | CHP | 1-BI | 2.84 | 0.04 | 0.12 | 0.024 |
| Example 15 | CHP | 1-BI | 2.84 | 0.04 | 0.12 | 0.013 |
| Example 16 | TBHP | 1-BI | 2.85 | 0.03 | 0.12 | 0.047 |
| Example 17 | TBHP | 1-BI | 2.85 | 0.03 | 0.12 | 0.024 |
| Example 18 | TBHP | 1-BI | 2.85 | 0.03 | 0.12 | 0.013 |

TABLE 4

| Composition | Open time (min) | Redox Cure Shore A > 30 @ 48 hrs. |
|---|---|---|
| Example 13 | 80 | Yes |
| Example 14 | 100 | Yes |
| Example 15 | 110 | Yes |
| Example 16 | 130 | Yes |
| Example 17 | 140 | Yes |
| Example 18 | 160 | No |

Examples 19-24

The procedure generally described for preparing Example 1 was repeated, according to the compositions listed in Table 5, wherein, after the base was homogeneously dispersed, 0.90 grams SOCAL filler was added and the mixture again manually stirred for 1 minute. Open Times and Redox Cure results are listed in Table 6.

A photoinitiator can be added to the compositions to make Examples 19 to 24.

TABLE 5

| | Composition | | | | | | |
|---|---|---|---|---|---|---|---|
| | | | Quantities (grams) | | | | |
| Composition | Hydro-peroxide | Base | PTE-1 | Hydro-peroxide | DVE-3/TAC | Base | SOCAL |
| Example 19 | CHP | Pyrazole | 2.84 | 0.04 | 0.12 | 0.020 | 0.90 |
| Example 20 | CHP | 3-MP | 2.84 | 0.04 | 0.12 | 0.025 | 0.90 |
| Example 21 | CHP | 1-MP | 2.84 | 0.04 | 0.12 | 0.025 | 0.90 |
| Example 22 | TBHP | Pyrazole | 2.85 | 0.03 | 0.12 | 0.020 | 0.90 |
| Example 23 | TBHP | 3-MP | 2.85 | 0.03 | 0.12 | 0.025 | 0.90 |
| Example 24 | TBHP | 1-MP | 2.85 | 0.03 | 0.12 | 0.025 | 0.90 |

TABLE 6

| Composition | Open time (min) | Redox Cure Shore A > 30 @ 48 hrs. |
|---|---|---|
| Example 19 | >300 | No |
| Example 20 | 90 | Yes |
| Example 21 | >240 | No |
| Example 22 | 120 | Yes |
| Example 23 | 90 | Yes |
| Example 24 | 110 | No |

Examples 25-37 and Comparatives D-H

The procedure generally described for preparing Example 19 was repeated, according to the compositions listed in Table 7. Open Times and Redox Cure results are listed in Table 8.

A photoinitiator can be added to the compositions to make Examples 25 to 37.

TABLE 7

| Composition | (Hydro)peroxide | Base | Quantities (grams) | | | | |
|---|---|---|---|---|---|---|---|
| | | | PTE-1 | (Hydro)peroxide | DVE-3/TAC | Base | SOCAL |
| Example 25 | TBHP | Pyrazole | 3.14 | 0.03 | 0.13 | 0.019 | 0.90 |
| Example 26 | TBHP | 1-BMI | 3.14 | 0.03 | 0.13 | 0.048 | 0.90 |
| Example 27 | TBHP | 4-PI | 3.14 | 0.03 | 0.13 | 0.040 | 0.90 |
| Example 28 | TBHP | 1-MB | 3.14 | 0.03 | 0.13 | 0.037 | 0.90 |
| Example 29 | TBHP | DMI | 3.14 | 0.03 | 0.13 | 0.027 | 0.90 |
| Example 30 | TBHP | 3-MP | 3.14 | 0.03 | 0.13 | 0.020 | 0.90 |
| Example 31 | TBHP | 4-IP | 3.14 | 0.03 | 0.13 | 0.054 | 0.90 |
| Example 32 | CHP | DMA | 3.14 | 0.05 | 0.13 | 0.048 | 1.57 |
| Example 33 | CHP | DMA | 3.14 | 0.14 | 0.13 | 0.048 | 1.57 |
| Example 34 | CHP | DMA | 3.14 | 0.24 | 0.13 | 0.048 | 1.57 |
| Example 35 | CHP | DMPT | 3.14 | 0.05 | 0.13 | 0.048 | 1.57 |
| Example 36 | CHP | DMPT | 3.14 | 0.14 | 0.13 | 0.048 | 1.57 |
| Example 37 | CHP | DMPT | 3.14 | 0.24 | 0.13 | 0.048 | 1.57 |
| Comparative D | BPO | DMPT | 3.14 | 0.16 | 0.18 | 0.032 | 1.57 |
| Comparative E | TBPO | DMPT | 3.14 | 0.16 | 0.18 | 0.032 | 1.57 |
| Comparative F | BPO | DMA | 3.14 | 0.16 | 0.18 | 0.032 | 1.57 |
| Comparative G | TBPO | DMA | 3.14 | 0.16 | 0.18 | 0.032 | 1.57 |
| Comparative H | BPO | DMPT | 3.14 | 0.08 | 0.13 | 0.032 | 1.57 |

TABLE 8

| Composition | Open time (min) | Redox Cure Shore A > 30 @ 48 hrs. |
|---|---|---|
| Example 25 | 120 | Yes |
| Example 26 | 80 | Yes |
| Example 27 | 75 | Yes |
| Example 28 | 90 | Yes |
| Example 29 | 70 | Yes |
| Example 30 | 80 | Yes |
| Example 31 | 130 | Yes |
| Example 32 | >300 | No |
| Example 33 | >300 | No |
| Example 34 | 240 | Yes |
| Example 35 | >300 | No |
| Example 36 | >300 | No |
| Example 37 | 120 | Yes |
| Comparative D | 60 | No |
| Comparative E | >300 | No |
| Comparative F | >300 | No |
| Comparative G | >300 | No |
| Comparative H | 180 | No |

Examples 38-44

The procedure generally described for preparing Example 25 was repeated, wherein the hydroperoxide TBHP was substituted with Irgacure 819, according to the compositions listed in Table 9. Each Example was evenly split into three samples and held for 1 hour, 4 hours and 48 hours in the dark at 21° C., after which each sample was irradiated for 10 seconds at 450 nm, at a distance of approximately 1 cm, by means of the Elipar S-10 lamp. In all instances, all samples were fully cured.

A hydroperoxide can be added to the compositions to make Examples 38 to 44.

TABLE 9

| Composition | Initiator | Base | Quantities (grams) | | | | |
|---|---|---|---|---|---|---|---|
| | | | PTE-1 | I-819 | DVE-3/TAC | Base | SOCAL |
| Example 38 | I-819 | Imidazole | 2.82 | 0.03 | 0.12 | 0.020 | 0.90 |
| Example 39 | I-819 | 1-BI | 2.82 | 0.03 | 0.12 | 0.047 | 0.90 |
| Example 40 | I-819 | DMI | 2.82 | 0.03 | 0.12 | 0.029 | 0.90 |
| Example 41 | I-819 | Pyrazole | 2.82 | 0.03 | 0.12 | 0.020 | 0.90 |
| Example 42 | I-819 | 3-MP | 2.82 | 0.03 | 0.12 | 0.025 | 0.90 |
| Example 43 | I-819 | 1-MP | 2.82 | 0.03 | 0.12 | 0.025 | 0.90 |
| Example 44 | I-819 | None | 2.82 | 0.03 | 0.12 | 0 | 0.90 |

Examples 45-47

Part A and Part B sealant compositions were prepared as follows.

Part A

I-819 was pre-dissolved in PTE-2 in a glass jar by means of a heated roller mixer at approximately 70° C. for 2 hours, according to the compositions listed in Table 10-A. The mixture was transferred to a mixing cup, to which DMI, SOCAL and A-R202 was added and the composition homogeneously dispersed at 2000 rpm for 1 minute at 21° C. using a model "ARV-310" planetary vacuum mixer from Thinky Corporation, Tokyo, Japan Part B TAC, DVE-3, CHP, A-R202 and FEB, according to the amounts listed in Table 10-B, were added to a mixing cup and homogeneously dispersed at 2000 rpm for 1 minute at 21° C. using the planetary vacuum mixer.

The Part A and the corresponding Part B compositions were manually mixed together at 21° C. according to the quantities listed in Table 10-C. The resultant Open Time, Tensile Strength, Elongation and Hardness of the sealant Examples are reported in Table 10-D.

TABLE 10-A

| Composition | Composition (grams) | | | | |
|---|---|---|---|---|---|
| | PTE-2 | I-819 | DMI | SOCAL | A-R202 |
| 45-A | 24.737 | 0.263 | 0.083 | 6.308 | 0.575 |
| 46-A | 24.737 | 0.263 | 0.166 | 8.651 | 0.596 |
| 47-A | 24.742 | 0.257 | 0.244 | 13.605 | 0.63 |

TABLE 10-B

| Composition | Composition (grams) | | | | |
|---|---|---|---|---|---|
| | TAC | DVE-3 | CHP | A-R202 | FEB |
| 45-B | 3.853 | 4.688 | 0.719 | 0.741 | 0 |
| 46-B | 2.608 | 3.174 | 0.973 | 0.5404 | 0.027 |
| 47-B | 3.323 | 4.044 | 1.86 | 0.738 | 0.035 |

TABLE 10-C

| Example | Part A | | Part B | |
|---|---|---|---|---|
| | Composition | Amount (grams) | Composition | Amount (grams) |
| Example 45 | 36-A | 31.997 | 36-B | 1.830 |
| Example 46 | 37-A | 34.420 | 37-B | 1.979 |
| Example 47 | 38-A | 39.440 | 38-B | 2.121 |

TABLE 10-D

| Example | Irradiated | Open Time (min) | Tensile Strength (psi/kPa) | Elongation (%) | Hardness (Shore A) |
|---|---|---|---|---|---|
| Example 45 | No | 130 | not fully cured | not fully cured | not fully cured |
| Example 45 | Yes | NA | 320/2,206 | 167 | 51.0 |
| Example 46 | No | 65 | 152/1,048 | 449 | 34.5 |
| Example 46 | Yes | NA | 314/2,165 | 138 | 55.0 |
| Example 47 | No | 45 | 467/3,220 | 758 | 46.5 |
| Example 47 | Yes | NA | 324/2,234 | 264 | 53.0 |

NA = Not Applicable

Examples 48-53

The procedure generally described in Example 38 was repeated, wherein the base was substituted with hydroperoxide according to the compositions listed in Table 11. Redox Cure and Photo Cure results are listed in Table 12.

TABLE 11

| Composition | Initiator | Hydroperoxide | Quantities (grams) | | | | |
|---|---|---|---|---|---|---|---|
| | | | PTE-1 | I-819 | DVE-3/TAC | Peroxide | SOCAL |
| Example 48 | I-819 | TBHP | 3.30 | 0.065 | 0.14 | 0.020 | 0.90 |
| Example 49 | I-819 | TBHP | 3.30 | 0.065 | 0.14 | 0.046 | 0.90 |
| Example 50 | I-819 | TBHP | 3.30 | 0.065 | 0.14 | 0.092 | 0.90 |

TABLE 11-continued

| | | | Composition | | | | |
|---|---|---|---|---|---|---|---|
| | | Hydro- | Quantities (grams) | | | | |
| Composition | Initiator | peroxide | PTE-1 | I-819 | DVE-3/TAC | Peroxide | SOCAL |
| Example 51 | I-819 | CHP | 3.30 | 0.065 | 0.14 | 0.033 | 0.90 |
| Example 52 | I-819 | CHP | 3.30 | 0.065 | 0.14 | 0.079 | 0.90 |
| Example 53 | I-819 | CHP | 3.30 | 0.065 | 0.14 | 0.159 | 0.90 |

TABLE 12

| Composition | Open Time (min) | Redox Cure Shore A > 30 @ 48 hrs. | Photo Cure Shore A > 30 @ 10 sec. |
|---|---|---|---|
| Example 48 | 100 | Yes | Yes |
| Example 49 | 80 | Yes | Yes |
| Example 50 | 60 | Yes | Yes |
| Example 51 | >180 | No | Yes |
| Example 52 | >180 | No | Yes |
| Example 53 | >180 | Yes | Yes |

Various modifications and alterations of this disclosure may be made by those skilled the art without departing from the scope and spirit of the disclosure, and it should be understood that this invention is not to be unduly limited to the illustrative embodiments set forth herein.

What is claimed is:

1. A composition comprising:
   a polythiol;
   at least one unsaturated compound comprising more than one carbon-carbon double bond, carbon-carbon triple bond, or a combination thereof, wherein each carbon-carbon double bond or carbon-carbon triple bond is a terminal group;
   a photoinitiator;
   an organic hydroperoxide, and
   a nitrogen-containing base comprising an imidazole or pyrazole.

2. The composition of claim 1, wherein the organic hydroperoxide comprises at least one of cumene hydroperoxide, tert-butyl hydroperoxide, or tert-amyl hydroperoxide.

3. The composition of claim 1, wherein the photoinitiator is a cleavage-type photoinitiator.

4. The composition of claim 1, wherein the polythiol is monomeric.

5. The composition of claim 1, wherein the polythiol is oligomeric or polymeric.

6. The composition of claim 5, wherein the polythiol is a polythioether oligomer or polymer or a polysulfide oligomer or polymer.

7. The composition of claim 1, wherein the at least one unsaturated compound comprises two carbon-carbon double bonds, and wherein the curable composition further comprises a second unsaturated compound comprising three carbon-carbon double bonds.

8. A method of making a polymer network, the method comprising:
   providing the composition of claim 1;
   and at least one of:
      exposing the composition to light to at least partially cure the composition; or
      allowing the composition to at least partially cure at ambient temperature.

9. A polymer network preparable from the composition of claim 1, wherein at least some of the thiol groups in the polythiol and carbon-carbon double bonds, carbon-carbon triple bonds, or a combination thereof have reacted to form thioether groups.

10. A cured sealant comprising the polymer network of claim 9.

11. The composition of claim 1, wherein the organic hydroperoxide comprises at least one of cumene hydroperoxide, tert-butyl hydroperoxide, or tert-amyl hydroperoxide, the photoinitiator is a cleavage-type photoinitiator, the polythiol is monomeric, oligomeric or polymeric, and the at least one unsaturated compound comprises two carbon-carbon double bonds, and wherein the curable composition further comprises a second unsaturated compound comprising three carbon-carbon double bonds.

12. A composition comprising:
   a polythiol;
   at least one unsaturated compound;
   a photoinitiator; and
   an organic hydroperoxide,
   wherein either (a) the organic hydroperoxide is other than methyl ethyl ketone peroxide, or (b) the composition also comprises a nitrogen-containing ring and further wherein the at least one unsaturated compound comprises two carbon-carbon double bonds, wherein each carbon-carbon double bond is a terminal group, and wherein the curable composition further comprises a second unsaturated compound comprising three carbon-carbon double bonds.

13. The composition of claim 12, wherein the ring portion of the nitrogen-containing ring is unsubstituted or substituted with at least one halogen, alkyl, arylalkylenyl, or aryl.

14. The composition of claim 13, wherein the nitrogen-containing ring is an imidazole or pyrazole.

15. The composition of claim 1, wherein the ring portion of the nitrogen-containing ring is either unsubstituted or substituted with at least one halogen, alkyl, arylalkylenyl, or aryl.

16. The composition of claim 1, wherein each carbon-carbon double bond or carbon-carbon triple bond is a terminal group of a linear aliphatic compound.

17. The composition of claim 12, wherein each carbon-carbon double bond is a terminal group of a linear aliphatic compound.

* * * * *